United States Patent [19]

Ramos et al.

[11] Patent Number: 5,641,678
[45] Date of Patent: Jun. 24, 1997

[54] SERUM-FREE CULTURE MEDIUM FOR DROSPHILA INSECT CELLS

[75] Inventors: Luciano Ramos, Lower Gwynedd; Amy Anne Murnane, Phoenixville; Melvin Susumu Oka, Spring City, all of Pa.

[73] Assignee: SmithKline Beecham Corporation, Philadelphia, Pa.

[21] Appl. No.: 483,634

[22] Filed: Jun. 7, 1995

Related U.S. Application Data

[63] Continuation of Ser. No. 183,585, Jan. 18, 1994, abandoned.
[51] Int. Cl.⁶ .................................................. C12N 5/00
[52] U.S. Cl. .................................................. 435/404; 435/407
[58] Field of Search ............................ 435/240.3, 240.31, 435/240.2, 240.21, 240.4, 240.54, 240.1; 424/520, 529, 531

[56] References Cited

U.S. PATENT DOCUMENTS 4,786,599  11/1988  Chessebeuf et al. .............. 435/240.31
5,024,947  6/1991  Ihlow et al. ....................... 435/240.31

OTHER PUBLICATIONS

Gibco Catalog 1990 pp. 69–70.
Grace, Nature vol. 195 pp. 788–789 (1962).

*Primary Examiner*—David M. Naff
*Assistant Examiner*—Jhung-Won Colby
*Attorney, Agent, or Firm*—Jeffrey A. Sutton; Herbert H. Jervis; Edward T. Lentz

[57]  ABSTRACT

The invention provides serum-free media for the culture of drosophila insect cells. The serum-free media of the invention comprise a basal medium to which is added yeast hydrolysate, and albumin or dextran. In another embodiment of the invention, albumin hydrolysate is added to the basal medium, in addition to the aforementioned compounds.

15 Claims, No Drawings

SERUM-FREE CULTURE MEDIUM FOR DROSPHILA INSECT CELLS

This is a continuation of application Ser. No. 08/183,585, filed Jan. 18, 1994, now abandoned.

FIELD OF THE INVENTION

The present invention relates to the field of media for the culture of cells. More particularly the present invention relates to media for the culture of insect cells.

BACKGROUND OF THE INVENTION

Beyond a basal nutrient mixture of salts, sugars, amino acids, and vitamins, cells in vitro have also been found to require for proliferation a supplement of poorly defined biological fluids or extracts. Because of availability and ease of storage, the most commonly used supplement is serum.

The use of serum in cell culture media, however, has several disadvantages. Serum is comparatively expensive. Since serum is not a defined component, different lots of serum may vary in the concentration of compounds present and thus result in unpredictable culture growth. Serum may also be contaminated with viruses or mycoplasmas. The protein in serum may complicate the purification of cell products from the culture medium.

In efforts to overcome the disadvantages of serum containing medium, researchers have attempted to provide serum-free media by substituting defined or better characterized components for serum. Unfortunately, the complexity of serum and the differing growth requirements of different types of cells has made it difficult to provide such media. For reviews on serum-free media for insect cell culture see Mitsuhashi (1982) "Continuous Cultures of Insect Cell Lines in Media Free of Sera" Appl. Ent Zool. 17: 575–581; and Goodwin, "Growth of insect cells in serum-free media" in *Techniques in the Life Sciences, Setting Up and Maintenance of Tissue and Cell Cultures*, Elsevier Scientific Publishers Ireland, Ltd., (1985) pp. C109/1–C109/28. Lazar et al. (1987) Dev. Biol. Stand. 96: 315–323 (Abstract) reports a serum-free medium for the culture of *Aedes aegypti* cells that contains bovine serum albumin.

The fruit fly *Drosophila melanogaster* has for many years been the subject of intensive genetic analysis and various media have been developed for the culture of Drosophila cells. Inlow et al. (1989) J. Tissue Culture Methods 12: 13–16 discloses a serum-free medium for culture of Drosophila cells that contains yeast hydrolysate and a lipid emulsion. For media containing serum, see Shields et al. (1975) J. Embryol. exp. Morph. 33: 159–175; Lengyel et al. "Methods with Insect Cells in Suspension Culture II. *Drosophila melanogaster*" in Methods in Cell Biol. volume 10, pp. 195–208, (1975); Shields and Sang (1977) Drosophila Information Service, volume 52, page 161; Cross and Sang (1978) J. Embryol. exp. Morph. 45: 161–172; Sang (1981) "Drosophila Cells and Cell Lines" in Advances in Cell Culture volume 1, pp 125–182; and Ueda and Miyake (1987) In Vitro Cellular & Developmental Biology 23: 707–711.

There have been a few reports of serum-free media containing dextran or β-cyclodextrin, however, the reported media are for the culture of mammalian cells. Pietrzkowski et al (1988) Folia Histochemica et Cytobiologica 26: 123–132 report a serum-free medium for the culture of chick embryo cell containing dextran. Pietrzkowski and Korohoda (1988) Folia Histochemica et Cytobiologica 26: 143–154 report a serum-free medium containing dextran for the culture of chick embryo fibroblasts. Ohmori (1988) Journal of Immunological Methods 112: 227–233 reports a serum-free medium which is able to support primary antibody responses by cultured murine lymphocytes. This medium is based on a basal medium supplemented with β-cyclodextrin, insulin, transferrin, albumin, low density lipoprotein, putrescine and alanine.

A serum-free medium for large-scale culture of insect (*Spodoptera frugiperda*) cells was reported in Maiorella et al., (1988) Biotechnology 6: 1406–1410. In addition to a basal medium, the medium contained yeast extract, cod liver oil polyunsaturated fatty acid methyl esters, cholesterol and Tween. Murhammer and Goochee (1988) Biotechnology 6: 1411–1418 discloses a medium for the culture of *Spodoptera frugiperda* that contains serum.

It is an object of the invention to provide serum-free media for the culture of insect cells. It is also object of the invention to provide serum-free media for the culture of insect cells transformed to produce recombinant products that increase product yield. It is yet another object of the invention to provide serum-free media for the culture of Drosophila cells.

SUMMARY OF THE INVENTION

The present invention provides serum-free media for the culture of insect cells. The invention is more particularly pointed out in the appended claims and is described in its preferred embodiments in the following description.

DETAILED DESCRIPTION OF THE INVENTION

The serum-free media of the invention are useful for the culture of insect cells. The media of the invention have been found to be useful in the culture of Drosophila cells, and should have utility in the culture of a wide variety of insect cells. Cells may be grown in batch and continuous culture with the serum-free media of the invention. Drosophila cells grown in the media of the invention reach higher cell density and show increased recombinant product secretion when compared to Drosophila cells grown in a serum-containing medium. The media of the invention have a low protein content which is advantageous for culturing cells for the production of recombinant proteins. The low protein content of the media reduces the amount of unwanted proteins that have to be separated from the protein product during purification of the protein product. Additionally, the media may be made at a much lower cost than media containing serum.

The cell culture media are prepared by adding supplements to a basal medium designed for insect cell culture. The media are prepared accordance with standard procedures for preparing cell culture media.

A preferred basal medium for use in the serum-free media of the invention is described in Example 1. Other suitable basal media include Grace's (Gibco, Grand Island, N.Y.) and Schneider's (Gibco)

Supplements are then added to the basal medium. Yeast hydrolysate is added in the amount of from about 1 to about 10 grams per liter. Dextran or albumin are added in the amount of from about 0.1 to about 5 grams per liter. Albumin for use in the media is preferably bovine serum albumin, however, albumin from other species is also suitable. Dextran for use in the media is preferably dextran having a molecular weight of about 500,000 such as Dextran T-500. In one embodiment of the invention, lactalbumin hydrolysate is added in the amount of from about 0.2 to about 5 grams per liter, preferably in the amount of about 5 grams per liter.

The pH range of the media is preferably in the range of from about 6.3 to about 6.7. The osmolarity is preferably in the range of from about 320 to about 360 milliosmoles.

The basal medium may be stored as a powder at 4° C. for one year. The complete medium (basal medium with added supplements) in a liquid form may be stored at 4° C. for six months.

Preferred embodiments of the invention are described in the following Examples.

EXAMPLE 1

| BASAL MEDIA COMPONENTS SERUM-FREE MEDIA | |
| --- | --- |
| Components | Grams/Liter |
| MgSO4 7H2O | 4.40 |
| Potassium Glutamate | 7.88 |
| Sodium Glutamate | 6.53 |
| NaH2PO4 H2O (monobasic) | 0.78 |
| Glucose | 10.0 |
| Oxaloacetic Acid | 0.25 |
| Bis-Tris | 1.05 |
| L-aspartic acid | 0.30 |
| L-threonine | 0.50 |
| L-serine | 0.35 |
| L-asparagine | 0.30 |
| L-glutamine | 0.60 |
| L-proline | 0.40 |
| Glycine | 0.50 |
| L-alanine | 1.50 |
| L-valine | 0.40 |
| L-methionine | 0.25 |
| L-isoleucine | 0.25 |
| L-leucine | 0.40 |
| L-tyrosine | 0.25 |
| L-phenylalanine | 0.25 |
| B-alanine | 0.25 |
| L-histidine | 0.55 |
| L-tryptophan | 0.10 |
| L-arginine | 0.50 |
| L-lysine HCL | 0.85 |
| L-cysteine HCL | 0.20 |
| Choline chloride | 0.05 |
| CaCl2 2H2O | 1.00 |
| KHCO3 | 0.50 |
| 1M NaOH | as needed |

Preparation of Basal Medium:

The components in the basal medium are mixed and ball-mill ground to formulate a homogeneous powder. The powdered medium is then dispensed into 100 L packets and stored at 4° C. for up to one year.

For a final volume of 100 L:

Ninety liters of deionized-distilled water is measured into an appropriate mixing vessel. A 100 L packet of ball-mill ground powdered medium. (as described above) is added. The pH of the medium is adjusted to 6.6 using 10N NaOH. The volume of the medium is brought to 100 L by the addition of water. The medium may then be sterilized by membrane filtration using a 0.2 micron cellulose acetate filter.

EXAMPLE 2

Medium MR-D1 contains the basal medium of Example 1 supplemented with 5 grams per liter TC lactalbumin hydrolysate (Difco, Detroit, Mich.), 1 gram per liter TC yeastolate (Difco, Detroit, Mich.) and 1 gram per liter bovine serum albumin (Amour, Kankakee, Ill.). The medium is prepared as follows:

For a final volume of 100 liters

1. Measure 90 liters of deionized-distilled water into an appropriate mixing vessel.
2. Add one 100 L packet of ball-mill ground powdered media (from Example 1).
3. Add 500 grams of TC lactalbumin hydrolysate, mix until dissolved.
4. Add 100 grams of TC yeastolate, mix until dissolved.
5. Add 100 grams of bovine serum albumin, mix until dissolved.
6. Adjust pH to 6.6 using 10N NaOH.
7. Add water to bring final volume to 100 liters and mix thoroughly.
8. Filter sterilize using a 0.2 micron cellulose acetate filter.
9. Check osmolarity and record.
10. Store at 4° C. for up to six months.

EXAMPLE 3

Medium MR-D2 contains the basal medium of Example 1 supplemented with 5 grams per liter TC yeastolate (Difco, Detroit, Mich.) and 1 gram per liter bovine serum albumin (Amour, Kankakee, Ill.). The medium is prepared as follows:

For a final volume of 100 L

1. Measure 90 liters of deionized-distilled water into an appropriate mixing vessel.
2. Add 100 L packet of ball-mill ground powdered media (from Example 1).
3. Add 500 grams of TC yeastolate, mix until dissolve.
4. Add 100 grams of bovine serum albumin, mix until dissolved.
5. Adjust pH to 6.6 using 10N NaOH.
6. Add water to bring final volume to 100 liters and mix thoroughly.
7. Filter sterilize using a 0.2 micron cellulose acetate filter.
8. Check osmolarity and record.
9. Store at 4° C. for up to six months.

EXAMPLE 4

Medium MR-D3 contains the basal medium of Example 1 supplemented with 5 grams per liter TC yeastolate (Difco, Detroit, Mich.) and 1 gram per liter of Dextran T-500 (Pharmacia, Piscataway, N.J.). The medium is prepared as follows:

For a final volume of 100 L

1. Measure 90 liters of deionized-distilled water into an appropriate mixing vessel.
2. Add one 100 L packet of ball-mill ground powder media (from Example 1).
3. Add 500 grams of TC yeastolate, mix until dissolved.
4. Add 100 grams of Dextran T-500, mix until dissolved.
5. Adjust pH to 6.6 using 10N NaOH.
6. Add water to bring final volume to 100 liters and mix thoroughly.
7. Filter sterilize using a 0.2 micron cellulose acetate filter.
8. Check osmolarity and record.
9. Store at 4° C. for up to six months.

EXAMPLE 5

Comparison of Growth of Drosophila (ACC086) cells in M3+5%FBS, MR-D1, or MR-D2, and the production of gp120 in these media Drosophila cells (cell line ACC086) ($2\times10^6$ cells per milliliter) that had been transfected to express human immunodeficiency virus-1 protein gp120 were cultured in M3 medium with 5% fetal bovine serum (FBS); MR-D1, the medium of Example 2; or MR-D2, the medium of Example 3. M3 medium is the medium described in Example 1 with 1 gram per liter Yeastolate (Difco, Detroit, Mich.) added. Each of the media also contained 300 μg/ml hygromycin B (HB), an antibiotic. Cells were cultured for 14 days and the number of cells and amount of gp120 were determined at intervals.

As shown in Table 1, after seven days, cells grown in M3+5% FBS had a density of $1.6\times10^7$ and the gp120 concentration was 956 ng/ml. Cells grown in MR-D1 medium and MR-D2 media had densities of $1.7\times10^7$ and $1.8\times10^7$, respectively, and gp120 concentrations of 916 ng/ml and 912 ng/ml, respectively. However, after 14 days of culture, cell density and gp120 production in MR-D1 and MR-D2 media were significantly higher than in M3+5% FBS medium. In MR-D1 medium, cell density was $3.0\times10^7$ and the gp120 concentration was 1,962 ng/ml. In MR-D2 medium, cell density was $2.7\times10^7$ and the concentration of gp120 was 2,750 ng/ml. In contrast the density of cells grown in M3+5% FBS medium was $2.1\times10^7$ and the concentration of gp120 was 1,207 ng/ml.

TABLE 1

| | M3 + 5% FBS +300 ug/ml HB CELL # ... GP120 | MR-D1 +300 ug/ml HB CELL # ... GP120 | MR-D2 +300 ug/ml HB CELL # ... GP120 |
|---|---|---|---|
| 7D | 1.6e7 ... 956 nG/ml | 1.7e7 ... 916 nG/ml | 1.8e7 ... 912 nG/ml |
| 14D | 2.1e7 ... 1,207 nGml | 3.0e7 ... 1,962 nG/ml | 2.7e7 ... 2,750 nG/ml |

EXAMPLE 6

Long Term Study Comparing the Growth Of Drosophila Cells (Cell Line ACC086) And Production Of gp120 In Either MR-D2 or MR-D3 Media Drosophila cells ($2\times10^6$ cells per milliliter) that had been transfected to express human immunodeficiency virus-1 protein gp120 (cell line ACC086) were cultured in a 250 ml SP flask containing 120 ml of either MD-R2, the medium of Example 3; or MD-R3, the medium of Example 4. Cells were passaged at 7 day intervals, and were cultured through 41 passages.

After 25 passages, in MR-D2 medium there were approximately $23\times10^6$ cells. In MR-D3 medium there were approximately $19\times10^6$ cells per milliliter. After 26 passages, gp120 production was about 550 ng/ml in MR-D2 and 700 ng/ml in MR-D3. After 30 passages there were approximately $20\times10^6$ cells per milliliter in MR-D2 and approximately $21\times10^6$ cells per milliliter in MR-D3. After 33 passages there were approximately $20\times10^6$ cells per milliliter in both MR-D2 and MR-D3 media, and gp120 production was about 750 ng/ml in MR-D3 and 650 ng/ml in MR-D3.

After 35 passages there were approximately $19\times10^6$ cells per milliliter in MR-D2 medium, and approximately $21\times10^6$ cells per milliliter in MR-D3 medium. gp120 production was about 550 ng/ml in MR-D2 medium, and about 500 ng/ml in MR-D3 medium. After 39 passages there were approximately $20\times10^6$ cells per milliliter in MR-D2 cells, and approximately $19\times10^6$ cells per milliliter in MR-D3 medium. gp120 production was about 375 ng/ml in MR-D2 medium and about 525 ng/ml in MR-D3 medium. After 40 passages, there were approximately $21\times10^6$ cells per milliliter in MR-D2 medium, and approximately $19\times10^6$ cells per milliliter in MR-D3 medium. gp120 production was about 300 ng/ml in MR-D2 medium and about 425 ng/ml in MR-D3 medium.

Over an extended period of time, cell growth in these serum-free media was consistent, although recombinant gp120 product production decreased slightly.

We claim:

1. A serum-free Drosophila culture medium consisting essentially of:

(a) a synthetic basal medium consisting essentially of

| Components | Concentration (g/L) |
|---|---|
| MgSO$_4$.7H$_2$O | 4.40 |
| Potassium Glutamate | 7.88 |
| Sodium Glutamate | 6.53 |
| NaH$_2$PO$_4$.H$_2$O (monobasic) | 0.78 |
| Glucose | 10.0 |
| Oxaloacetic Acid | 0.25 |
| Bis-Tris | 1.05 |
| L-aspartic acid | 0.30 |
| L-threonine | 0.50 |
| L-serine | 0.35 |
| L-asparagine | 0.30 |
| L-glutamine | 0.60 |
| L-proline | 0.40 |
| Glycine | 0.50 |
| L-alanine | 1.50 |
| L-valine | 0.40 |
| L-methionine | 0.25 |
| L-isoleucine | 0.25 |
| L-leucine | 0.40 |
| L-tyrosine | 0.25 |
| L-phenylalanine | 0.25 |
| B-alanine | 0.25 |
| L-histidine | 0.55 |
| L-tryptophan | 0.10 |
| L-arginine | 0.50 |
| L-lysine HCL | 0.85 |
| L-cysteine HCL | 0.20 |
| Choline chloride | 0.05 |
| CaCl$_2$.2H$_2$O | 1.00 |
| KHCO$_3$ | 0.50 |
| 1M NaOH | to provide a pH of about 6.3 to about 6.7 |

(b) from about 1 to about 10 grams per liter of yeast hydrolysate; and
   (c) from about 0.1 to about 5 grams per liter of dextran or albumin.

2. The medium of claim 1 wherein yeast hydrolysate is present in the amount of 2 grams per liter.

3. The medium of claim 1 wherein yeast hydrolysate is present in the amount of 5 grams per liter.

4. The medium of claim 1 wherein dextran is present in the amount of 1 gram per liter.

5. The medium of claim 4 wherein dextran is dextran having a molecular weight of about 500,000.

6. The medium of claim 1 wherein albumin is present in the amount of 1 gram per liter.

7. The medium of claim 6 wherein said albumin is bovine serum albumin.

8. The medium of claim 1 further consisting essentially of from about 0.2 to about 5 grams per liter of albumin hydrolysate.

9. The medium of claim 8 wherein said albumin hydrolysate is lactalbumin hydrolysate.

10. A serum-free Drosophila culture medium consisting essentially of:

(a) a synthetic basal medium consisting essentially of

| Components | Concentration (g/L) |
|---|---|
| $MgSO_4 \cdot 7H_2O$ | 4.40 |
| Potassium Glutamate | 7.88 |
| Sodium Glutamate | 6.53 |
| $NaH_2PO_4 \cdot H_2O$ (monobasic) | 0.78 |
| Glucose | 10.0 |
| Oxaloacetic Acid | 0.25 |
| Bis-Tris | 1.05 |
| L-aspartic acid | 0.30 |
| L-threonine | 0.50 |
| L-serine | 0.35 |
| L-asparagine | 0.30 |
| L-glutamine | 0.60 |
| L-proline | 0.40 |
| Glycine | 0.50 |
| L-alanine | 1.50 |
| L-valine | 0.40 |
| L-methionine | 0.25 |
| L-isoleucine | 0.25 |
| L-leucine | 0.40 |
| L-tyrosine | 0.25 |
| L-phenylalanine | 0.25 |
| B-alanine | 0.25 |
| L-histidine | 0.55 |
| L-tryptophan | 0.10 |
| L-arginine | 0.50 |
| L-lysine HCL | 0.85 |
| L-cysteine HCL | 0.20 |
| Choline chloride | 0.05 |
| $CaCl_2 \cdot 2H_2O$ | 1.00 |
| $KHCO_3$ | 0.50 |
| 1M NaOH | to provide a pH of about 6.3 to about 6.7 |

(b) about 2 grams per liter of yeast hydrolysate;

(c) about 1 gram per liter serum albumin; and (d) about 5 grams per liter albumin hydrolysate.

11. The medium of claim 10 wherein said serum albumin is bovine serum albumin, and said albumin hydrolysate is lactalbumin hydrolysate.

12. A serum-free Drosophila culture medium consisting essentially of:

(a) a synthetic basal medium consisting essentially of

| Components | Concentration (g/L) |
|---|---|
| $MgSO_4 \cdot 7H_2O$ | 4.40 |
| Potassium Glutamate | 7.88 |
| Sodium Glutamate | 6.53 |
| $NaH_2PO_4 \cdot H_2O$ (monobasic) | 0.78 |
| Glucose | 10.0 |
| Oxaloacetic Acid | 0.25 |
| Bis-Tris | 1.05 |
| L-aspartic acid | 0.30 |
| L-threonine | 0.50 |
| L-serine | 0.35 |
| L-asparagine | 0.30 |
| L-glutamine | 0.60 |
| L-proline | 0.40 |
| Glycine | 0.50 |
| L-alanine | 1.50 |
| L-valine | 0.40 |
| L-methionine | 0.25 |
| L-isoleucine | 0.25 |
| L-leucine | 0.40 |
| L-tyrosine | 0.25 |
| L-phenylalanine | 0.25 |
| B-alanine | 0.25 |
| L-histidine | 0.55 |
| L-tryptophan | 0.10 |
| L-arginine | 0.50 |
| L-lysine HCL | 0.85 |
| L-cysteine HCL | 0.20 |
| Choline chloride | 0.05 |
| $CaCl_2 \cdot 2H_2O$ | 1.00 |
| $KHCO_3$ | 0.50 |
| 1M NaOH | to provide a pH of about 6.3 to about 6.7 |

(b) about 5 grams per liter of yeast hydrolysate; and (c) about 1 gram per liter of albumin.

13. The medium of claim 12 wherein said albumin is bovine serum albumin.

14. A serum-free Drosophila culture medium consisting essentially of:

(a) a synthetic basal medium consisting essentially of

| Components | Concentration (g/L) |
|---|---|
| $MgSO_4 \cdot 7H_2O$ | 4.40 |
| Potassium Glutamate | 7.88 |
| Sodium Glutamate | 6.53 |
| $NaH_2PO_4 \cdot H_2O$ (monobasic) | 0.78 |
| Glucose | 10.0 |
| Oxaloacetic Acid | 0.25 |
| Bis-Tris | 1.05 |
| L-aspartic acid | 0.30 |
| L-threonine | 0.50 |
| L-serine | 0.35 |
| L-asparagine | 0.30 |
| L-glutamine | 0.60 |
| L-proline | 0.40 |
| Glycine | 0.50 |
| L-alanine | 1.50 |
| L-valine | 0.40 |
| L-methionine | 0.25 |
| L-isoleucine | 0.25 |
| L-leucine | 0.40 |
| L-tyrosine | 0.25 |
| L-phenylalanine | 0.25 |
| B-alanine | 0.25 |
| L-histidine | 0.55 |
| L-tryptophan | 0.10 |
| L-arginine | 0.50 |
| L-lysine HCL | 0.85 |
| L-cysteine HCL | 0.20 |
| Choline chloride | 0.05 |
| $CaCl_2 \cdot 2H_2O$ | 1.00 |
| $KHCO_3$ | 0.50 |
| 1M NaOH | to provide a pH of about 6.3 to about 6.7 |

(b) about 5 grams per liter of yeast hydrolysate; and (c) about 1 gram per liter of dextran.

15. The medium of claim 14 wherein said dextran is dextran having a molecular weight of approximately 500,000.

* * * * *